United States Patent [19]

Barikosky

[11] Patent Number: 5,981,821
[45] Date of Patent: Nov. 9, 1999

[54] DRESSING PRODUCT WITH A CALCIUM ALGINATE MATRIX AND METHOD OF PRODUCTION OF THE SAME

[75] Inventor: Michel Barikosky, Nanterre, France

[73] Assignee: Societe Precis, Nanterre, France

[21] Appl. No.: 08/969,030

[22] Filed: Nov. 12, 1997

[30] Foreign Application Priority Data

Nov. 13, 1996 [FR] France ................................. 96 13802

[51] Int. Cl.⁶ ........................................................ A61F 13/00
[52] U.S. Cl. .............................. 602/41; 602/48; 424/445; 424/480; 428/221
[58] Field of Search ........................ 602/41, 48; 424/445, 424/480; 428/221

[56] References Cited

U.S. PATENT DOCUMENTS 5,718,916  2/1998  Scherr ..................................... 424/445

FOREIGN PATENT DOCUMENTS

| 2663229 | 12/1991 | France . |
|---|---|---|
| 2671486 | 7/1992 | France . |
| 653341 | 5/1951 | United Kingdom . |
| 1328088 | 9/1969 | United Kingdom . |
| WO 92/22285 | 12/1992 | WIPO . |
| WO 96/13282 | 5/1996 | WIPO . |

*Primary Examiner*—John G. Weiss
*Assistant Examiner*—Kelvin Hart
*Attorney, Agent, or Firm*—Graham & James LLP

[57] ABSTRACT

The dressing for a chronic wound with biological liquid, comprises a matrix of calcium alginate associated with at least one alginate of a multivalent metal, with the exception of magnesium. The multivalent metal alginate is produced from sodium alginate which is extruded through a die disposed in a coagulation bath of a soluble salt solution of the multivalent metal. The multivalent metal alginate is associated with the calcium alginate matrix by means of a textile technique.

7 Claims, No Drawings

DRESSING PRODUCT WITH A CALCIUM ALGINATE MATRIX AND METHOD OF PRODUCTION OF THE SAME

The present invention firstly relates to a dressing product, or dressing, for chronic wounds with biological liquid, for moist wounds, particularly deep ones, for example, exuding cavities such as ulcers, scars or other post-operative wounds.

Calcium alginate is a spinnable polymer like any metal alginate of the group of multivalent metals with the exception of magnesium.

If a dressing comprising a mesh of calcium alginate fibres is considered which is applied to a wound which is losing matter or biological liquid (blood or exudate) the dressing begins by absorbing the biological liquid which suints or exudes, the water molecules of the liquid becoming interspersed between the macromolecules of the alginate. Once swelled by absorption the dressing is subjected to gelling by ionic exchange. In the case of calcium alginate fibres, these give up $Ca^{2+}$ ions to the biological liquid which gives up $Na^+$ ions to them. As equilibrium becomes established between the calcium and sodium the alginate fibres partially lose their crystalline structure. The gelling of the dressing causes the wound to dry and prevents adhesion to the subjacent tissues.

If a dressing comprising a matrix of calcium alginate associated with a layer of sodium alginate is considered, as taught by FR-A-2 663 229, from the time the layer of sodium alginate is placed in contact with the biological fluid the sodium alginate, which is a monovalent metal alginate, passes into solution, which inhibits the calcium alginate matrix, which begins to lose $Ca^{2+}$ ions and to take up $Na^+$ ions, before the whole is reduced to the gel state by the continuation of this ion exchange.

It will be noted at this point that the function of the sodium alginate layer is to promote the gelling of the calcium alginate layer on a wound which is only slightly exudative.

However, in order for a chronic wound to heal properly it is necessary to restore the physiology of its cells, ie to overcome their deficit in essential ionised metal mineral elements which previously, ie before appearance of the wound, were low in quantity. This is a matter of so-called trace elements and more particularly multivalent metals (zinc, manganese, copper, selenium, etc) except for magnesium.

The Applicant has thus ventured to substitute the soluble monovalent metal alginate layer associated with the calcium alginate matrix of a prior art dressing with the alginate of a multivalent metal, with the exception of magnesium, which is insoluble by reason of ionic bridges created by the multivalent metal but of which the molecules will nevertheless be able to be dissociated by the monovalent cations and ions of the biological liquid, in order to propose a dressing with the capability of physiological restoration.

The invention thus relates to a dressing product for a chronic wound with biological liquid, comprising a calcium alginate matrix associated with at least one alginate of a multivalent metal, with the exception of magnesium.

When the biological liquid of the wound comes into contact with the dressing the metal ions of one of the two alginates are released, without dissolution, before the ions of the other alginate are also released to the point of hydroelectrolytic equilibrium between the ions of the biological liquid, on the one hand, and the ions of the two alginates, on the other, thus restoring the physiology of the cells of the wound by provision of ions of the multivalent metal, ie the trace element. Thus the dormant metabolism of the cells at the base of the wound can be reawakened.

The multivalent metal of the alginate associated with the calcium alginate matrix is advantageously selected from the group comprising zinc, manganese, copper, selenium.

Of course, a plurality of alginates of a plurality of multivalent metals respectively can be associated with the calcium alginate matrix.

The invention also relates to a method of production of a dressing product for a chronic wound with biological liquid, comprising a calcium alginate matrix associated with at least one alginate of a multivalent metal, with the exception of magnesium, wherein the multivalent metal alginate is produced from sodium alginate which is extruded through a die disposed in a coagulation bath of a chloride solution of the multivalent metal.

The invention also relates to a method of production of a dressing product for a chronic wound with biological liquid, comprising a calcium alginate matrix associated with at least one alginate of a multivalent metal, with the exception of magnesium, wherein the multivalent metal alginate is associated with the calcium alginate matrix by means of a textile technique.

The invention will be better understood with the aid of the following description of the production method, chemical and mechanical, of the dressing of the invention and with the aid of the attached FIGS. 1 to 7 illustrating the results of experiments detailed hereinunder.

Chemical Aspects

Calcium alginate fibres, which are purchased commercially or can be produced, may be used for the calcium alginate.

The alginate of a multivalent metal, except magnesium, will generally be produced in the following manner (more precise examples will be given later). The process begins with hydrosoluble sodium alginate. It is extruded through a die which is disposed in a coagulation bath of a soluble salt solution, for example, a chloride, of the metal concerned. By ionic exchange between the sodium and the metal the desired metal alginate is obtained which is insoluble and in the form of fibres.

Mechanical Aspects

With the aim of obtaining so-called physiological concentrations it is preferred to resort to textile techniques which make it possible to control the quantities of fibrillate alginate while ensuring the homogeneous nature of the dressing.

The components of the dressing can each be a non-woven fabric, a woven fabric, flocks, powder, threads, a band of fibres, stitching threads, etc.

1) Two non-woven fabrics 1.1 Fibres of the two alginates are thoroughly mixed before being agglutinated into a non-woven sheet.

1.2 Alternatively a non-woven web of each alginate is folded over on itself to form a sheet, the two sheets are superimposed and the layered composite assembly is subjected to needle bonding before a compress is obtained.

2) One non-woven fabric and one woven (or knitted) fabric

A non-woven sheet of a first alginate and a woven (knitted) sheet of the second alginate are superimposed. After needle bonding a compress is obtained. The calcium alginate sheet can be the woven or the non-woven sheet.

3) A non-woven fabric and flocks

To a non-woven sheet of a first alginate are attached flocks of the second alginate by a bonding agent which is compatible with wounds. An adhesive is advantageously used as the bonding agent.

4) A non-woven fabric and powder

The process is the same as above for the flocks.

5) A non-woven fabric and threads

Threads of a first alginate are disposed on one side or the other of a non-woven sheet of a second alginate or between two non-woven sheets of one or two other alginates and the assembly is subjected to needle bonding. A compress is thus obtained.

Threads

Three techniques can be considered:

a) Continuous threads can be used having one or a plurality of filaments, obtained with a die;

b) threads can be used obtained from strands of fibres stretched to detach therefrom the fibres which are then subjected
   to the action of a twisting machine (spinning machine technique) or
   to the action of a spinning head (turbine) for entwining the detached fibres and for forming threads (open-end technique);

c) it is possible to use threads obtained by the DREFF method well known to the person skilled in the art in order to wind the fibres around one or a plurality of continuous threads.

6) A non-woven fabric and a band of fibres

A band of fibres of a first alginate is superimposed on a non-woven sheet of a second alginate and the assembly is subjected to needle bonding to obtain a compress.

7) A woven fabric and flocks

The method is the same as for a non-woven fabric with the only difference being that the sheet is woven.

8) A woven fabric and powder

The method is the same as for a non-woven fabric with the only difference being that the sheet is woven.

9) A non-woven fabric and stitching threads

Stitching from a stitching machine is applied to a non-woven sheet of a first alginate and fixed with the aid of a bonding agent such as, for example, for a non-woven fabric and flocks.

10) A woven fabric and threads

A woven sheet of a first alginate either has stitching of a second alginate fixed to it or threads of a second alginate are associated therewith, for example, according to the Jacquard method.

Reference has been made to this point to a dressing with only two alginates. Of course, it is possible to envisage all the possible compositions of calcium alginate, on the one hand, and of one or a plurality of alginates of multivalent metals, except magnesium, on the other.

Two examples of the production of mixtures of fibres will now be presented.

EXAMPLE 1

Four types of alginate fibres were produced of the same fineness, in this case 230 dTex, and in the same spinning conditions with identical parameters in short-ratch spinning equipment and
  a concentration of sodium alginate solution of 6%,
  a concentration of salt in the coagulation bath of 1.5M,
  initial concentrations of ions chelated by the alginate expressed in g of ion for 100 g of dry fibre as follows:
    calcium alginate . . . 7.95% $Ca^{2+}$
    zinc alginate . . . 11.87% $Zn^{2+}$
    copper alginate . . . 10.24% $Cu^{2+}$
    manganese alginate . . . 14.74% $Mn^{2+}$ The kinetics of release of the metal ions were achieved by incubation of the different fibres with physiological solution (NaCl 9%), by measuring the concentration of the ion concerned in the solution after 1 h, 12 h and 24 h. Differences of affinity in the ions for the alginate exist in the following order.

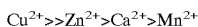

These differences are shown by the graphs of FIGS. 1 and 2 showing the kinetics of release of the ions of the pure metal alginates, ie the evolution over time, expressed in hours h, ratios Q in % of the quantities released expressed in g per 100 g of fibre (FIG. 1), and ratios R in % of the quantities released with respect to the initial quantities (FIG. 2).

At 24 h the calcium alginate has released 83% of its calcium ions, the zinc alginate 40% of its zinc ions, the copper alginate 25% of its copper ions, the manganese alginate 59% of its manganese ions. These rates correspond to maximums (the curves are virtually horizontal) and this time of 24 h corresponds to the average time a dressing remains on a wound.

After cutting the fibres into flocks the following mixture was produced:
  calcium alginate . . . 76%
  zinc alginate . . . 8%
  copper alginate . . . 8%
  manganese alginate . . . 8%

The release kinetics were achieved as before, at each time stage the concentration of the four ionic types present simultaneously being measured.

The result are illustrated by the graphs of FIGS. 3 and 4 illustrating the release kinetics of the associated metal alginate ions (calcium, zinc, manganese, copper) and more particularly the evolution of the ratios Q (FIG. 3) and R (FIG. 4) as defined above. These results show that the concentrations of released ions vary with respect to the results of FIGS. 1 and 2. There are competition mechanisms (agonism and antagonism).

At 24 h the mixture released 92% of its calcium ions, 60% of its zinc ions, 6% of its copper ions and 96% of its manganese ions.

The control of the concentrations of trace elements in the wound thus depends on:
  the initial types in the mixture,
  the initial quantities in the mixture,
  the control of the mixture of fibres.

EXAMPLE 2

Alginate fibres were produced of the same types and in the same conditions as in Example 1.

Three mixtures A, B, C were produced by stitching with a thread of metal alginate on a non-woven fabric of calcium alginate.

|  | A | B | C |
|---|---|---|---|
| Calcium alginate | 99.96% | 99.96% | 99.97% |
| Zinc alginate | 0.04% | | |
| Copper alginate | | 0.04% | |
| Manganese alginate | | | 0.003% |

The release kinetics were achieved as in Example 1. The results are illustrated by the graphs of FIGS. 5–7 showing the release kinetics of the associated metal alginate ions, ie the evolution of the ratios R as defined above for the three mixtures A (FIG. 5), B (FIG. 6) and C (FIG. 7).

The results obtained show that it is possible to control very low (physiological) concentrations of trace elements and that the kinetics with two metal ionic types differ from those obtained previously since the competition mechanisms are more simple.

It will also be noted that in addition to the nature of the trace element, its initial concentration influences the kinetics: this is shown by the fact that the ionic equilibrium rests on the affinity coefficients of the different ions for the alginate (Example 1) and on the concentrations of the different types.

I claim:

1. Dressing product for a chronic wound with biological liquid, comprising a calcium alginate matrix associated with at least one alginate of a multivalent metal, with the exception of magnesium.

2. Dressing product according to claim 1, wherein a plurality of alginates of a plurality of multivalent metals are associated with the calcium alginate matrix.

3. Dressing product according to claim 1, wherein the multivalent metal of the alginate associated with the calcium alginate matrix is selected from the group comprising zinc, manganese, copper, selenium.

4. Method of production of a dressing product for a chronic wound with biological liquid, comprising a calcium alginate matrix associated with at least one alginate of a multivalent metal, with the exception of magnesium, wherein the multivalent metal alginate is produced from sodium alginate which is extruded through a die disposed in a coagulation bath of a soluble salt solution of the multivalent metal.

5. Method of production of a dressing product for a chronic wound with biological liquid, comprising a calcium alginate matrix associated with at least one alginate of a multivalent metal, with the exception of magnesium, wherein the multivalent metal alginate is associated with the calcium alginate matrix by means of a textile technique.

6. Method of production according to claim 5, wherein in order to associate the calcium alginate matrix with the multivalent metal alginate, a non-woven sheet of calcium alginate and of multivalent metal alginate in one of the forms of the assembly comprising a non-woven sheet, a woven-sheet, flocks, powder, threads, stitching, a band of fibres is initially used.

7. Method of production according to claim 5, wherein in order to associate the calcium alginate matrix with the multivalent metal alginate, a woven sheet of calcium alginate and of multivalent metal alginate in one of the forms of the assembly comprising flocks, powder, threads is initially used.

* * * * *

UNITED STATES PATENT AND TRADEMARK OFFICE
CERTIFICATE OF CORRECTION

PATENT NO : 5,981,821
DATED : November 9, 1999
INVENTOR(S): Michel BARIKOSKY and Philippe MAINGAULT It is certified that error appears in the above-identified patent and that said Letters Patent is hereby corrected as shown below:

On the title page, item [75],
Inventors: Michel Barikosky, Nanterre, France
Philippe Maingault, Fontevraud L'Abbaye - France Signed and Sealed this Twelfth Day of December, 2000

Attest:

Q. TODD DICKINSON

Attesting Officer

Director of Patents and Trademarks